(12) United States Patent
Cheng

(10) Patent No.: US 6,581,233 B1
(45) Date of Patent: Jun. 24, 2003

(54) ELECTRICALLY OPERABLE TOOTHBRUSH

(75) Inventor: Rocky Cheng, Shatin (HK)

(73) Assignee: Perfect Steam Appliance Ltd., Shatin (HK)

( * ) Notice: Subject to any disclaimer, the term of this patent is extended or adjusted under 35 U.S.C. 154(b) by 0 days.

(21) Appl. No.: 09/517,440

(22) Filed: Mar. 2, 2000

(30) Foreign Application Priority Data

Aug. 25, 1999 (DE) .......................................... 199 40 369

(51) Int. Cl.⁷ .............................................. A46B 13/02
(52) U.S. Cl. .............................. 15/28; 15/22.1; 15/22.2
(58) Field of Search ................... 15/22.1, 22.2, 15/28

(56) References Cited

U.S. PATENT DOCUMENTS

| | | |
|---|---|---|
| 3,524,088 A | 8/1970 | Ryckman et al. |
| 3,562,566 A * | 2/1971 | Kircher |
| 5,504,959 A | 4/1996 | Yukawa et al. |

FOREIGN PATENT DOCUMENTS

| | | |
|---|---|---|
| DE | 19520303 A1 | 6/1995 |
| DE | 19717334 C1 | 4/1997 |
| EP | 0651978 A1 | 5/1995 |
| EP | 628 291 B1 | 5/1999 |
| JP | 08000356 A | 1/1996 |

* cited by examiner

*Primary Examiner*—Randall E. Chin
(74) *Attorney, Agent, or Firm*—Scully, Scott, Murphy & Presser

(57) ABSTRACT

An electrically operable toothbrush, in particular an electrically operable toothbrush which includes an oscillatingly rotatable brush head, with the brush head being connected with a drive shaft, so as to be supported for rotation about its longitudinal axis. An electric motor is arranged in a handgrip of the toothbrush and a gearing having the input thereof connected with the electric motor and the output thereof with the drive shaft.

8 Claims, 5 Drawing Sheets

ELECTRICALLY OPERABLE TOOTHBRUSH

BACKGROUND OF THE INVENTION

1. Field of the Invention

The present invention relates to an electrically operable toothbrush, in particular an electrically operable toothbrush which includes an oscillatingly rotatable brush head, with the brush head being connected with a drive shaft, so as to be supported for rotation about its longitudinal axis. An electric motor is arranged in a handgrip of the toothbrush and a gearing having the input thereof connected with the electric motor and the output thereof with the drive shaft.

Electrical toothbrushes of that type are already widely employed in the practice and known from the literature. These toothbrushes consist, in general, of a handgrip in which there is located a storage battery, an electric motor and a gearing or power transmission which has an input connected with the electric motor. The gearing drives a drive shaft which is usually arranged so as to extend in parallel with the longitudinal axis of the elongate handgrip, and conducted outwardly from the upper and of the handgrip. Mountable on the drive shaft is a brush attachment which, in general, is exchangeable in nature.

The brush attachment, in turn, possesses a drive shaft which is directly connected with the drive shaft in the handgrip, so as to form an extended drive shaft. Furthermore, the brush attachment is equipped with a brush head, which is supported in a manner so as to be able to implement oscillatory rotational movements. The brush head is coupled with the drive shaft through the intermediary of a reversing mechanism. Hereby, the brush head is mostly orientated such that its central axis extends somewhat perpendicular to the longitudinal axis of the drive shafts. However, there also exist toothbrushes whose brush heads possess a central axis which is oriented in parallel with the longitudinal axis of the drive shafts.

2. Discussion of the Prior Art

An electrically operable toothbrush of that type, for example, is disclosed in German DE 39 37 854 A1. The toothbrush which is disclosed therein possesses essentially some of the basic features of the above-mentioned toothbrush construction. In particular, this known electrically operable toothbrush possesses an electric motor which is arranged in a handgrip, which motor through the interposition of a gearing device and a reversing mechanism actuated by the latter oscillatingly drives a rotatably supported brush head. The gearing device is constructed as a quadrilateral control linkage system which, at the input thereof, is driven through a spur gear arrangement by the electric motor, and at the output end thereof oscillatingly drives a drive shaft within angular range of about ±35°.

In addition to these known toothbrushes with oscillatingly rotatable brush heads, there also exist toothbrushes with brush heads which carry out swinging or pendulous movements, or also which superimpose two oscillatory movements. Toothbrushes of that type in general require a completely differently constructed gearing device in order to produce these brush head movements.

SUMMARY OF THE INVENTION

Accordingly, proceeding from the above-mentioned state-of-the-technology, it is an object of the present invention to provide an electrically operable toothbrush with an oscillatingly rotatable brush head which operates at an extremely high degree of efficiency, and the gearing drive, of which is almost noiseless during its operation.

The foregoing object is obtained through the provision of an electrically operable toothbrush in which the transmission or gearing has a first eccentric wheel positioned on a gear shaft which is essentially arranged perpendicular to the drive shaft, a second eccentric wheel positioned on the shaft, and a drive wheel which is coupled to the first and second eccentric wheels, wherein the first eccentric wheel is arranged in a circular recess in a holder for the drive shaft so as to be able to displace the drive shaft upwardly and downwardly, and wherein the second eccentric wheel is arranged in an oval recess in the holder in order to stabilize the lift or the stroke of the drive shaft.

The gearing which is employed in the inventive toothbrush as described above facilitates that on the one hand, there is obtained an extremely high degree of operating efficiency for the transmission or gearing, in effect, almost the total energy introduced from the electric motor is converted into the lift or stroke of the drive shaft, while moreover, this gearing operates almost noiselessly.

Advantageously, the first and second eccentric wheels are fastened in such a manner on the driving mechanism shaft, such that their eccentricities with regard to the driving mechanism shaft are oriented directly oppositely, whereby the eccentricity of the first eccentric wheel is greater than that of the second eccentric wheel so that the lift or stroke of the drive shaft is defined by the sum of the eccentricities of two eccentric wheels with regard to the driving mechanism.

Furthermore, it is advantageous to guide the drive shaft through the intermediary of one or more ball bearings located interiorly of the handgrip. Due to the lubricating effect of the ball bearings, there can be reduced any frictional, overheating and wear effects acting on the drive shaft.

BRIEF DESCRIPTION OF THE DRAWINGS

The above advantages and features as well as additional advantages and features of the invention, are now described hereinbelow in specific detail on the basis of a preferred embodiment of the invention, taken in conjunction with the accompanying drawings; in which.

DETAILED DESCRIPTION OF A PREFERRED EMBODIMENT

Figure 1:
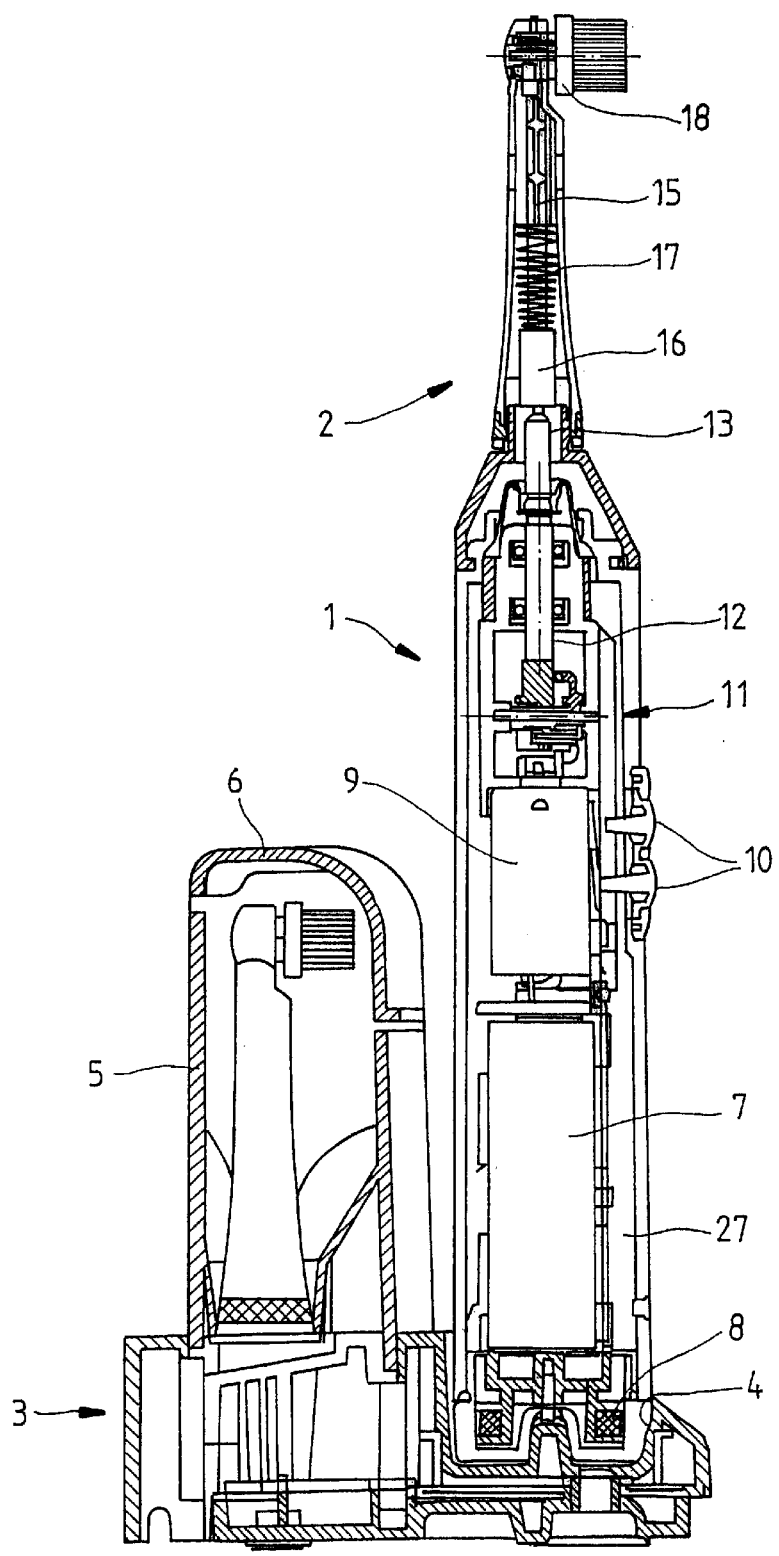
FIG. 1 illustrates a side view of an electrically operable toothbrush with a holder, shown in cross section pursuant to an embodiment of the present invention.

FIG. 1 illustrates initially an exemplary embodiment of an electrically operable toothbrush shown in overall representation in longitudinal cross-section. The electrically operable toothbrush consists essentially of a housing part 1 serving as a handgrip, a brush attachment 2 which is mountable thereon, and a holder 3 for the storage of the electrically operable toothbrush.

The holder 3 possesses a recess 4 for the releasable reception of the lower end of the handgrip 1 when the toothbrush is not used. The holder 3, for example, is fastenable by means of screws to a wall, or can be positioned on a supporting surface. Furthermore, there is also provided on the holder 3, a receiving compartment 5 for one or more brush attachments 5. Due to hygienic reasons, this receiving compartment is preferably closed off by means of an openable cover 6. The receiving compartment 5 serves for the storage of brush attachments for one or more common users of the electrically operable toothbrush.

Moreover, the holder 3 is equipped with a power supply connecting cable (not shown), so that for the stored handgrip 1, this enables the recharging of the storage battery or charger 7 which is arranged in the handgrip 1. The charging of the storage battery 7 is preferably inductively implemented by means of a coil 8 which is located within the lower end of the handgrip, and which is connected with the storage battery or charger. The holder 3 thus serves concurrently as a charging station for the electrically operable toothbrush. The inductive coupling is especially advantageous, inasmuch as with this embodiment there are no electrical contacts located on the handgrip 1 and also on the holder 3, through which the user could come into contact with the electrically operable toothbrush.

The battery or charger 7 is connected with the electric motor 9 which is similarly arranged in the handgrip, and serves the latter as a source of electrical current. Arranged on the outside of the handgrip 1, somewhat at the height of the electric motor 9, is a switch 10 for the switching on and off of the electric motor 9. The switch 10 is constructed; for example, as a toggle switch or as a slider switch.

The electric motor 9 is connected at its output end with the gearing 11 for the electrically operable toothbrush. The gearing 11, in turn, has its output end connected with a drive shaft 12 which is oriented generally in parallel with the longitudinal axis of the handgrip 1. The gearing 11 is more closely described hereinbelow on the basis of FIG. 4 through 6.

The drive shaft 12 extends outwardly from the upper end 13 of the handgrip 1. To this extension 13 of the drive shaft 1 the brush attachment 2 is attachable. Usually there are provided a plurality of brush attachments 2 for a single electrically operable toothbrush so that the latter can be commonly employed by a number of users. In order to be able to distinguish between the brush attachments 2 for the individual users, it is known to impart the brush attachments with colored rings 14 possessing different colors (as shown in FIGS. 2A and 2B).

The elongated brush attachment 2 similarly possesses a drive shaft 15, which extends in the extension of the drive shaft 12 of the handgrip 1 similarly in parallel with the longitudinal axis of the brush attachment 2 and of the handgrip 1. The drive shaft 15, at its lower end is equipped with a coupling element 16, which engages into the upper end of the extension 13 of the drive shaft 12, and which, for example, can be constructed generally spherically or ball-shaped, as a result of which the two drive shafts 12 and 15 are rotatably coupled with each other. At the attaching of the brush attachment 2, the coupling element 16 must be pressed inwardly against the force of a spring 17, in order to receive the extension 13. In order to remove the brush attachment 2 from the handgrip 1, it is sufficient to apply a small amount of force, in order to be able to release the coupling element 16 with the support of the spring force 17 from the extension 13 of the drive shaft 12.

Arranged at the upper end of the brush attachment 2 is brush head 18. This brush head 18 is arranged in a manner on the brush attachment such that its central axis is oriented generally perpendicular to the drive shaft 15. Instead of the orientation of the brush head 18 at a right angle relative to the longitudinal axis of the toothbrush it is also possible to contemplate other suitable angular positions.

Figures 2A, 2B:
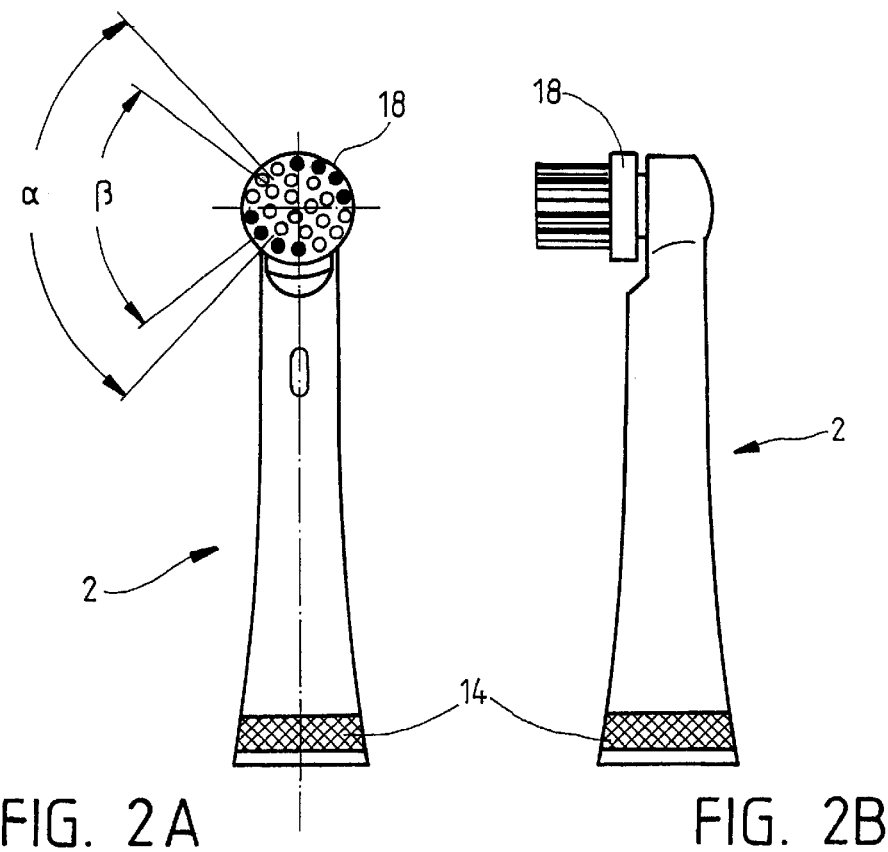
FIGS. 2A and 2B illustrate respectively, two side views of a brush attachment of the electrically operable toothbrush of FIG. 1.

As illustrated in FIG. 2A and 2B, the brush head 18 in the present exemplary embodiment has a circular contour. The brush head 18 is supported on the brush attachment 2 so as to be rotatably limited to an angular range α of about 100° towards both sides. The restriction in the angle of rotation is effected by a motion guide 19, 20, as explained in further detail hereinbelow on the basis of FIG. 3. Furthermore, the brush head 18 is oscillatably rotated by the gearing 11 in the handgrip 1 within an angular range β of about 79° towards both sides. The functioning of the gearing 11 is described in further detail hereinbelow.

Figure 3:
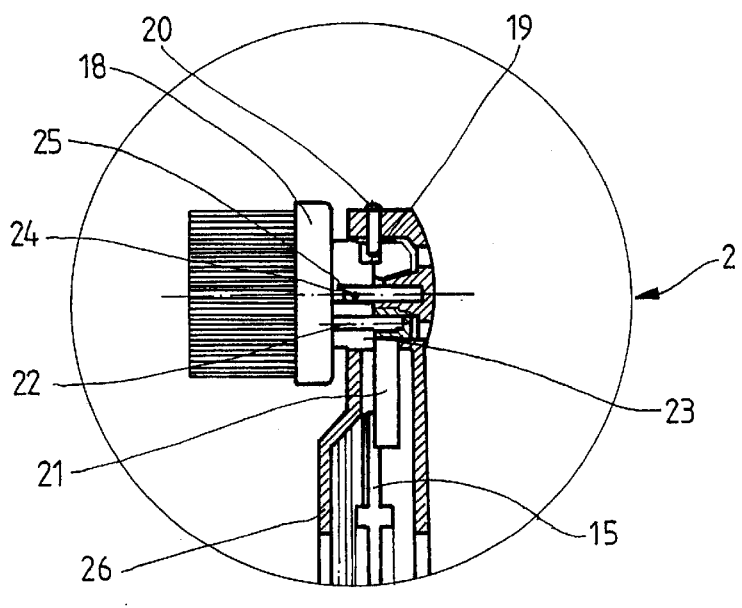
FIG. 3 illustrates, on an enlarged scale, a representation of a portion of the brush attachment of FIGS. 2A and 2B shown in cross section.

FIG. 3 discloses, on an enlarged scale, a fragmentary portion of the upper end of the brush attachment 2 in a cross-sectional view. Arranged at the upper end of the drive shaft 15 is a brush carrier 21. The brush carrier 21 is connected with an eccentric disk 23 which is seated on an eccentric shaft 22. The eccentric disk 23 is further seated on a main shaft 24 which is preferably constituted of metal, and which extends along the central axis of the brush head 18, whereby the eccentric shaft 22 and the main shaft 24 are oriented essentially perpendicular to the drive shaft 15. Fastened on the main shaft 24 is thus the brush head 18 with the aid of a guide sleeve 25. The two shafts 22, 24, as well as the brush carrier 21 are arranged in a brush head housing 26 of the brush attachment 2.

The eccentric disk 23 possesses a slit 19 which is oriented towards its upper side, and into which there engages a pin 20 which is attached to the brush head housing 26. The slit 19 serves as a motion guide for the brush head 18, and limits the possible range of rotation of the brush head for example, to about ±and 100°.

The drive shaft 15 which is connected with the drive shaft 12 of the handgrip 1, is displaced upwardly and downwardly by means of the gearing as described further on hereinbelow. As a result, the brush carrier 21 is thereby also moved upwardly and downwardly. The linear motion of the brush carrier 21 is converted with the aid of the eccentric arrangement 22, 23 and the guide pin 20 into an oscillatory rotational movement of the brush head 18 with an angular range of approximately ±79°.

By means of the gearing 11 of the present invention, oscillations of the brush head 18 are preferably set to be within, the range of 30 to 60 Hz, preferably of 45 to 50 Hz, which the user recommends as being comfortable during a cleaning or brushing procedure.

Figure 4:
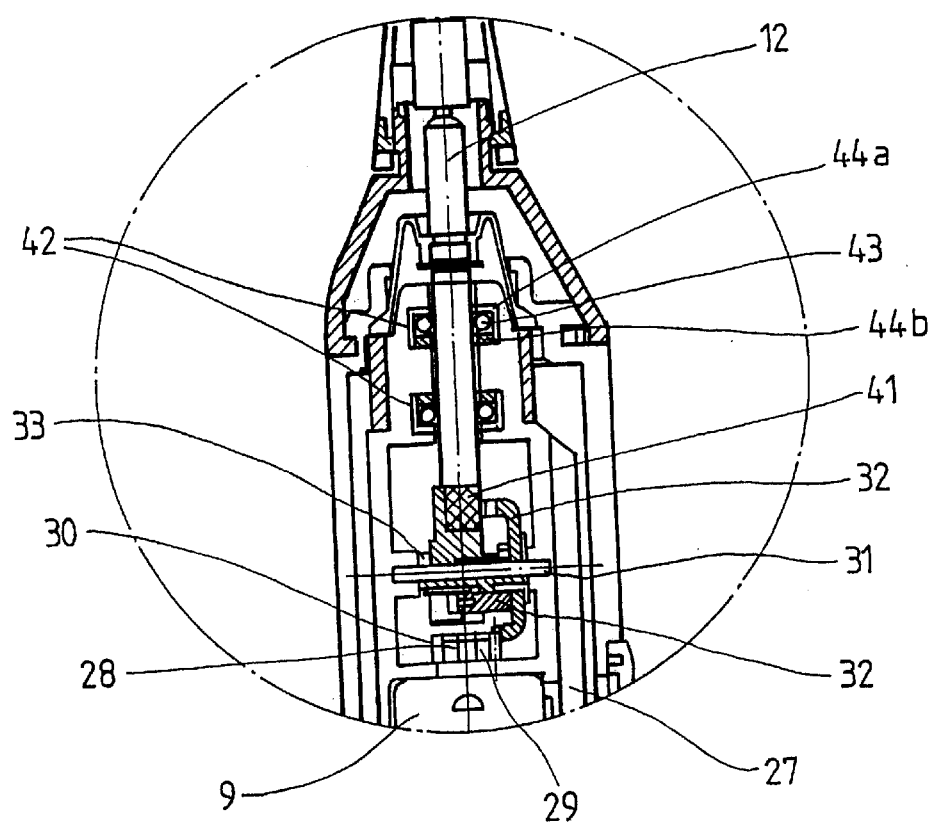
FIG. 4 illustrates, on an enlarged scale, a representation of the gearing or power transmission for the electrically operable toothbrush of FIG. 1.

Hereinbelow, there is subsequently described the construction of the gearing 11 on the basis of FIGS. 4 and 5.

The transmission or gearing 11 is driven by an electric motor 9 which is inserted into a motor mount 27 in the handgrip 1, and by means of the switch 10 can be switched on and off. The electric motor 9 is connected at its output with a motor shaft 28 which is arranged essentially in parallel with the longitudinal axis of the handgrip 1. Arranged on this motor shaft 20 through the interposition of a slipper clutch 29 is a gear 30. The gear 30 stands in engagement with the gearing 11 of the toothbrush.

The gearing 11 consists essentially of a gear drive shaft 31, which is oriented so as to be perpendicular to the longitudinal axis of the handgrip 1 and which forms the axis of the gearing 11, a driving wheel, respectively, a driving gear train 32, a first lower eccentric wheel 33 and a second upper eccentric wheel 34. The drive shaft 31 is preferably constituted from a hard steel. The drive wheel 32, in cross-section, has generally the form of an umbrella 35 with a hollow shaft 36 arranged on the central axis. The hollow shaft is seated on the gear drive shaft 36 and is fixedly connected therewith secured against relative rotation. The umbrella at its surrounding outer edge, possesses a gear toothing 37 which is in engagement with the gear train 30 on the motor shaft 28, so that a rotation of the motor shaft about the longitudinal axis of the handgrip 1 produces a rotation of the drive wheel 32 perpendicular relative thereto about the gear drive shaft 31.

The lower and the upper eccentric wheels 33, 34 are fastened secured against rotation on the shaft 36 of the drive wheel 32. The lower end of the drive shaft 12 is received or, respectively, fastened in a shaft retainer 41. In the shaft retainer 41 there is formed a receiving aperture 38 (referring to FIG. 5) which possesses a circular recess or cutout 39 and an oval recess or cutout 40. The lower eccentric wheel 33 is received in the circular recess 39 and the upper eccentric wheel 34 in the oval recess 40, of the receiving aperture 38, each in a precise fit and freely rotatable. The two eccentric wheels 33 and 34, the drive wheel 32 and the shaft retainer 41 are preferably constituted of a plastic material, such as for example, polyformaldehyde (POM). Received or, respectively retained in the shaft retainer 41 is the drive shaft 12. Alternatively thereto, the shaft retainer 41 can also be formed integrally with the drive shaft 12; in this instance, the receiving aperture 38 for the eccentric wheels 33, 34 of the gearing 11 provided directly in the lower end of the drive shaft 12.

The lower eccentric wheel 33 which is fixedly connected secured against relative rotation with the hollow shaft 36 of the drive wheel 32, due to its eccentric rotation about the gear drive shaft 31 in the recess 39 at the lower end of the drive shaft 12, produces an upward and downward movement of the shaft retainer 41, and thereby of the drive shaft 12. The upper eccentric wheel 34 serves for stabilizing the drive shaft 12 during the lifting motion the X-Y axis system caused by the lower eccentric wheel 33, whereby the X-axis is formed by the gear drive shaft 31 and the Y-axis by the drive shaft 12.

Figure 6:
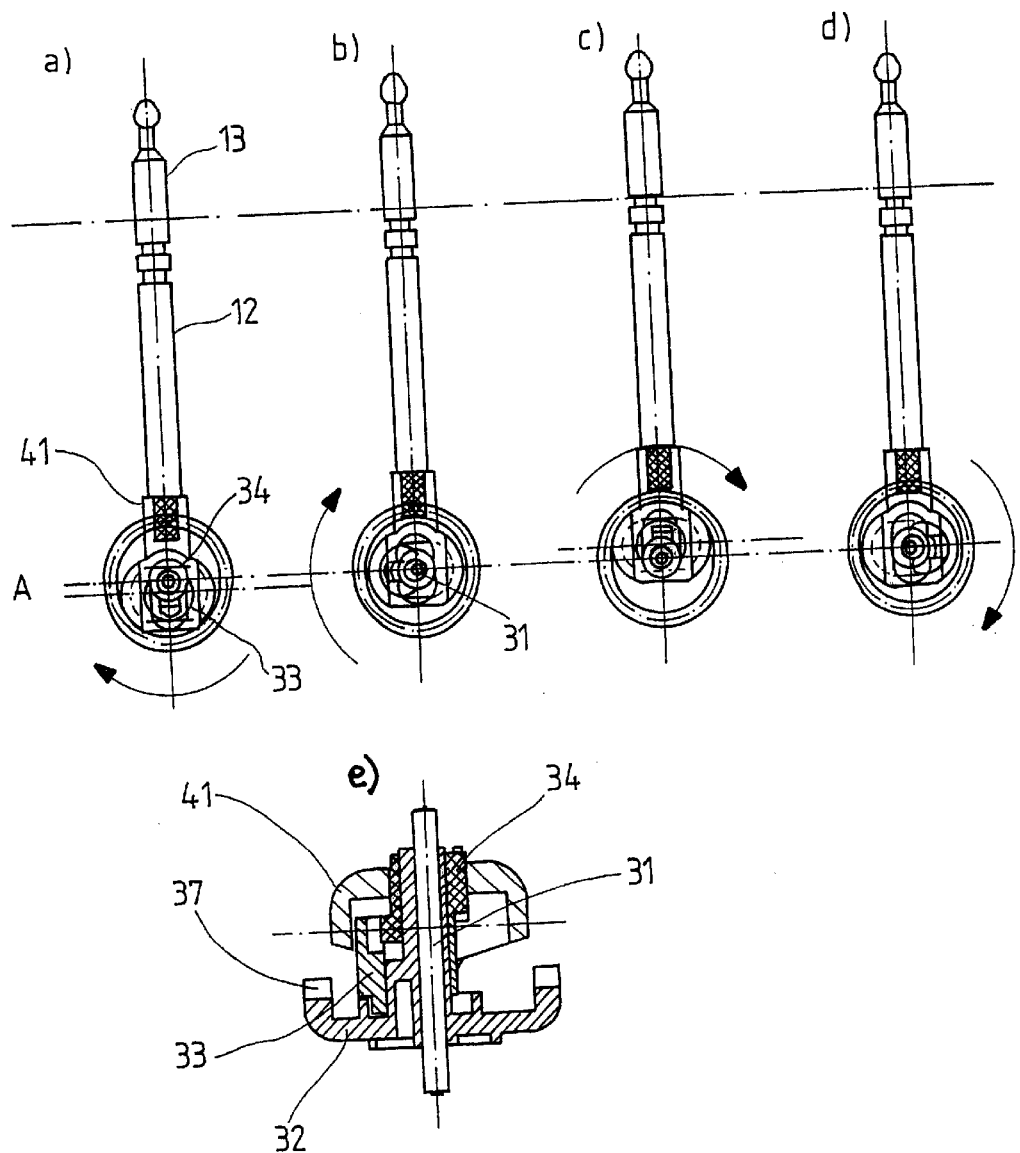
FIGS. 6A, 6B, 6C, 6D and 6E illustrate in a diagrammatic explanatory representation, the functioning of the gearing for the electrically operable toothbrush which is shown in FIGS. 4 and 5.

The functioning of the inventive gearing 11 is again more precisely explained with reference to FIG. 6 of the drawings.

Figure 5:
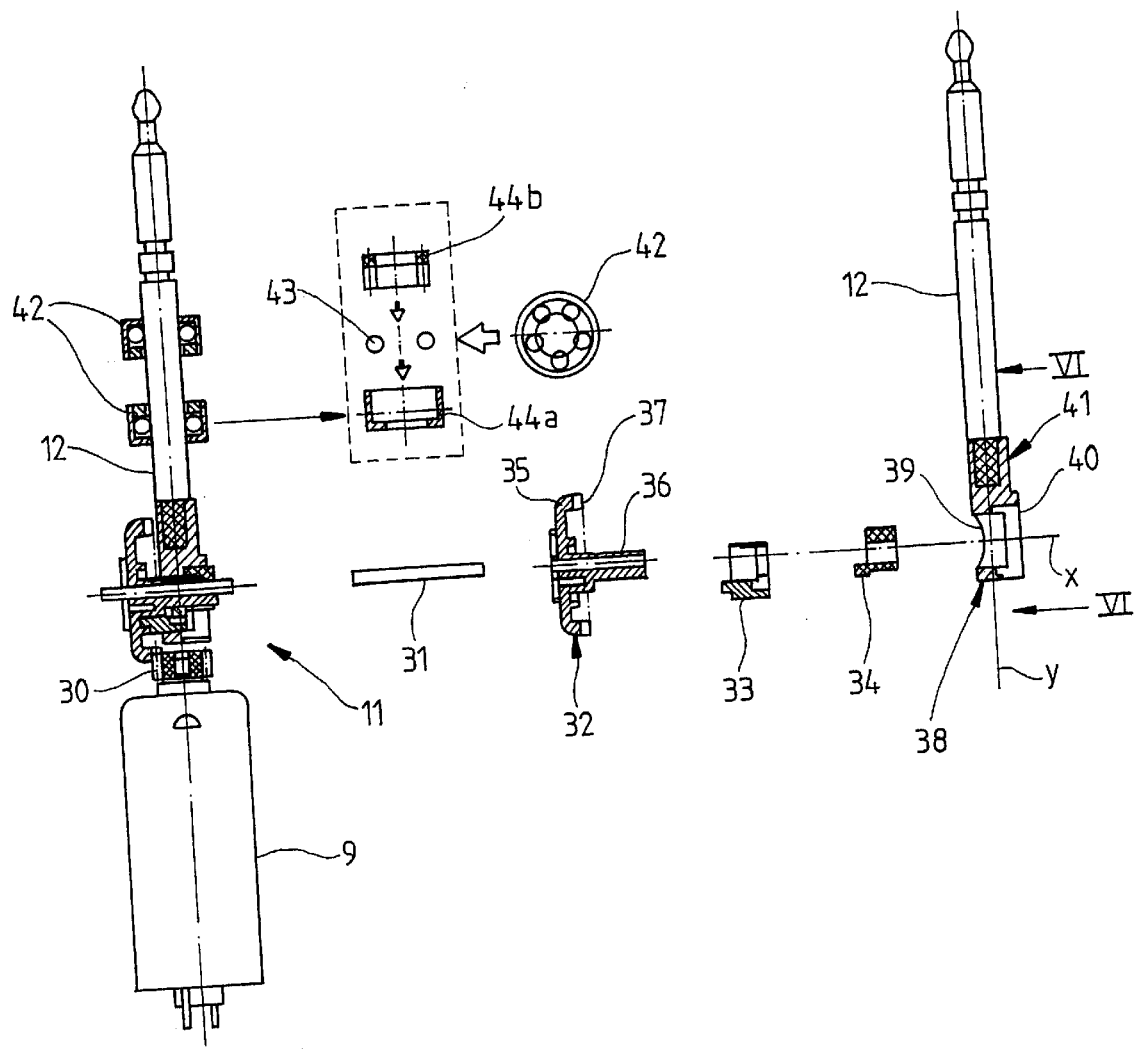
FIG. 5 illustrates in an exploded view, a diagrammatic representation explanatory of the construction of the gearing shown in FIG. 4 for the electrically operable toothbrush.

FIGS. 6A through 6D illustrate in four representations 6A through 6D of the gearing 11 and the drive shaft 12 in the side view pursuant to line VI—VI in FIG. 5, the different conditions of the cycle of motion of the upward and downward movement of the drive shaft 12 caused by the gearing 11. Additionally, there is again illustrated the drive 11 with its components shown in a plan view.

In the four representations of FIGS. 6A through 6D, the axis of the gear drive shaft 31 is presently located on the elevation line A. In the first representation FIG. 6A the lower eccentric wheel 33 is located in is lowest position, so that also the shaft retainer 41 and thereby the drive shaft 12 are pulled into their lowest position. The upper eccentric wheel 34, in contrast therewith, is located in its highest position. In the second representation FIG. 6B, in which shaft 31 has exerted a rotation through 90° in the clockwise direction relative to the position shown in FIG. 6A, the lower eccentric wheel 33 is positioned extended the furthest towards the left, so that the shaft retainer 41 and thereby also the drive shaft 12 assume their middle elevated position. The upper eccentric wheel 34 hereby finds itself in its furthest position extended towards the right. After a further quarter-rotation of the drive shaft 31 in the clockwise direction, the lower eccentric wheel 33 is located in its highest position, so that also the shaft retainer 41 and the drive shaft 12 have been displaced into their highest position (representation FIG. 6C). The upper eccentric wheel 34 in this instance, is located in its lowest position. The last representation FIG. 6D shows the lower eccentric wheel 33 in its furthest towards the rightward extended position, and the upper eccentric wheel 34 in its furthest leftward extended position, so that the shaft retainer 41 and the drive shaft 12 are located in their middle elevated position. Thereafter, the gear drive shaft 31 rotates further in the clockwise direction until there is again reached the constellation shown pursuant to representation FIG. 6A. The outward displacement of the upper eccentric wheel 34 is thus precisely opposite to that of the outward displacement of the lower eccentric wheel 33, so that the upward and downward motion of the drive shaft 12 is stabilized. The eccentricity of the lower eccentric wheel 33 is thereby naturally greater than the eccentricity of the upper eccentric wheel 34 so that the lift or stroke of the drive shaft 12 is determined by the sum of the eccentricities of the two eccentric wheels 33, 34 with respect to the gear drive shaft 31.

Through the thusly constructed power transmission from the electric motor 9 to the drive shaft 12 there is achieved an extremely high degree of efficiency, meaning there are encountered hardly any energy losses in the coupling or clutching through the gearing 11. Since the upper eccentric wheel 34 stabilizes the movement of the drive shaft 12, there are also not encountered any energy losses due to instabilities or fluctuations of the drive shaft 12, so that the energy which is introduced from the electric motor 9 is completely, or at least extensively, converted into the upward and downward movement of the drive shaft 12. In addition thereto, the thusly configured gearing 11 is also extremely low in noise during operation.

Referring again to FIG. 4 and 5, the drive shaft 12 is retained and guided in the interior of the handgrip 1 by means of, for example, two ball bearings 42 which are arranged along their longitudinal axis. As is particularly ascertainable from the detail in FIG. 5, the ball bearings 42 are each, respectively constituted from five steel balls 43 which are inserted in a plastic material housing 44. The plastic material housing 44 for the ball bearing 42; for example, consists of a polyformaldehyde material (POM). The ball bearing housing 44 is constructed in two parts and consists of socket 44b forming an inner race and a covering 44a forming the outer race. The inner race 44b is thereby constructed in such a manner that the balls 43 retained between the two races 44a and 44b protrude through the inner race 44b into the interior of the ball bearing housing 44, and come into contact with the drive shaft 12.

The ball bearings 42 are utilized in order to reduce the friction of the drive shaft, as well as any overheating and wear effects acting on the drive shaft, which can be encountered due to the high lift or stroke motion frequency of the drive shaft 12. This is in particular achieved through a lubricating effect of the ball bearings 42 for the drive shaft 12.

Instead of the above-described number of five balls 43 for each the ball bearings 42 it is also possible to contemplate constructions with a different number of balls 43. Moreover, the materials of the ball bearings 42 are not limited to those indicated above. Principally, all known ball bearings with different materials, sizes and the like can be employed for the electrically operable toothbrush pursuant to the present invention.

What is claimed is:

1. An electrically operable toothbrush including a brush head (18) which is connected with a drive shaft (12, 15), said brush head being supported so as to be rotatable about a longitudinal axis thereof; an electric motor (9) being arranged in a handgrip (1); and a gearing (11) which is coupled at an input with the electric motor (9) and at an output with the drive shaft (12, 15); wherein the gearing (11) includes a first eccentric wheel (33) located on a gear drive shaft (31) which is oriented substantially perpendicular to the drive shaft (12, 15), a second eccentric wheel (34) being located on the shaft (31) and a drive wheel (32) which is coupled with said first and second eccentric wheels (33, 34), the first eccentric wheel (33) being arranged in a circular recess (39) in a retainer (41) for the drive shaft (12, 15) so as to facilitate movement of the drive shaft (12, 15) upwardly and downwardly, and said second eccentric wheel (34) being arranged in an oval recess (40) in the retainer (41) so as to stabilize the lifting movement of the drive shaft (12, 15).

2. An electrically operable toothbrush according to claim 1, wherein said first and second eccentric wheels (33, 34) are fastened on the drive shaft 31 so that the eccentricities of said wheels are exactly oppositely directed, and wherein the eccentricity of the first eccentric wheel (33) is greater than the eccentricity of the second eccentric wheel (34).

3. An electrically operable toothbrush according to claim 1 or 2, wherein the eccentric wheels (33, 34), said gear drive wheel (32) and said shaft retainer (41) are each constituted of polyformaldehyde.

4. An electrically operable toothbrush according to claim 1, wherein the drive shaft (12, 15) is guided by at least one ball bearing (42).

5. An electrically operable toothbrush according to claim 1, wherein the retainer (41) is integrally formed with the drive shaft (12, 15).

6. An electrically operable toothbrush according to claim 1, wherein the longitudinal axis of the brush head (18) is oriented substantially perpendicular to the longitudinal axis of the drive shaft (12, 15).

7. An electrically operable toothbrush according to claim 6, wherein a reversing arrangement for converting the lifting movement of the drive shaft (12, 15) into the rotational movement of the brush head (18) is located intermediate the drive shaft (12, 15) and the brush head (18), and the reversing arrangement including eccentric disk (23) which is retained on a central main shaft (24) which carries the brush head as a rotational axis.

8. An electrically operable toothbrush according to claim 1, wherein there is provided an arrangement (19, 20) for guiding and limiting the rotational movement of the brush head (18).

\* \* \* \* \*